United States Patent [19]

Ali

[11] 4,309,184

[45] Jan. 5, 1982

[54] METHOD OF DETERMINING FOOD OR CHEMICAL ALLERGY AND INTOLERANCE

[76] Inventor: Majid Ali, 19 Edgemont Pl., Teaneck, N.J. 07666

[21] Appl. No.: 147,845

[22] Filed: May 8, 1980

[51] Int. Cl.³ .................... G01N 33/50; G01N 33/96
[52] U.S. Cl. .................... 23/230 B; 435/4; 435/16; 435/26
[58] Field of Search .................... 23/230 B; 435/4, 16, 435/26

[56] References Cited

U.S. PATENT DOCUMENTS

| 3,814,669 | 6/1974 | Goldenberg | 435/16 |
| 3,819,488 | 6/1974 | Rush | 435/26 X |
| 3,867,259 | 2/1975 | Forgione | 435/26 |
| 3,899,397 | 8/1975 | Morin | 435/16 |
| 4,003,795 | 1/1977 | Lamprecht | 435/26 |
| 4,006,061 | 2/1977 | Weeks | 435/26 |
| 4,024,021 | 5/1977 | Stavropoulos | 435/26 |
| 4,086,142 | 4/1978 | Huang | 435/4 |

OTHER PUBLICATIONS

Jacob J. Pruzansky, Journal of Immunology, 97 (6), 854–857, (1966).
Chemical Abstracts, 85:141234w (1976).

*Primary Examiner*—Sidney Marantz
*Attorney, Agent, or Firm*—Ostrolenk, Faber, Gerb & Soffen

[57] ABSTRACT

Food or chemical allergy and intolerance is determined by comparing an analysis for a given analyzable constituent of a polymorphonuclear leukocyte with and without incubation with the incriminated food or chemical. Allergy or intolerance to the food or chemical under consideration causes the leukocytes to break down releasing the analyzable constituent and permitting its presence to be determined.

10 Claims, No Drawings

METHOD OF DETERMINING FOOD OR CHEMICAL ALLERGY AND INTOLERANCE

BACKGROUND OF THE INVENTION

Food and chemical allergy and intolerance are difficult and poorly understood problems in clinical medicine. It has been estimated that up to 10% of the United States population has experienced symptoms attributable to hypersensitivity to food and chemicals and/or aggravation of their symptoms by elements in their diets. The diagnosis of food and chemical allergies remains an unsettled issue and the various tests heretofore employed are subject to numerous problems.

In addition to the RAST test, the test which has received the most attention for determining food and chemical allergies is known as the cytotoxic food test. This test is based on the fact that structural changes which are observable under the microscope are undergone by the living polymorphonuclear cells of the sensitive patient when exposed in vitro to the incriminated fool allergen. Such changes include cessation of motility, loss of pseudopods, vacuolation, and, in the most severe cases, disruption of the leukocytic cell membrane with the formation of so called "ghost cells". The cytotoxic food test was introduced into clinical use by Black in 1956. There have been several reports, before and since that time, concerning the morphologic alterations in segmented leukocytes induced by exposure to allergies. One notable exception to such reports was the experience of Franklin and Lowell who were unable to observe lysis of leukocytes after their exposure to ragweed allergens in patients with ragweed hypersensitivity.

In the cytotoxic food test, the polymorphonuclear cells are examined without any histochemical stains. The structural changes are often subtle and the evaluation of those changes is extremely subjective. As a result, wide variations in the results obtained by different observers has been a major source of dissatisfaction with this diagnostic technique.

A parallel diagnostic approach was investigated by monitoring the changes in the polymorphonuclear cell count in the circulating blood in patients with food allergies after they were challenged with the incriminated foods. A marked fall in the leukocyte count under these circumstances was considered a positive reaction. This diagnostic test is unsatisfactory because it is frequently negative in patients with known food allergies.

It is the object of this invention to provide a reliable in vitro test for determining food or chemical allergy or intolerance and thereby overcome the disadvantages of the prior art approaches. This and other objects of the invention will become apparent to those skilled in the art from the following detailed description of the invention.

SUMMARY OF THE INVENTION

This invention relates to an in vitro test for determining food or chemical allergy and intolerance and more particularly to a test which involves analyzing for a given analyzable constituent of a polymorphonuclear leukocyte with and without challenging the leukocyte with the incriminated food or chemical and comparing the results.

DESCRIPTION OF THE PREFERRED EMBODIMENTS

The principle of the in vitro test for food and chemical allergy and intolerance of the present invention approaches the diagnosis of these difficult problems from a totally different perspective from that of the prior art. It is based on the recognition of two facts. First, the polymorphonuclear leukocytes have a rich content of various enzymes, most notably SGOT (serum glutamic oxaloacetic transaminase), SGPT (serum glutamic pyruvic transaminase), LDH (lactic dehydrogenase), and many other substances such as lipids, proteins and carbohydrates. Secondly, a certain percentage of the polymorphonuclear leukocytes, largely determined by the degree of hypersensitivity, will undergo lysis after incubation with the incriminating food or chemical substance resulting in the release of these intracellular constituents. Many procedures are known for the qualitative and quantitative analysis of these various enzymes, lipids, proteins, carbohydrates and the like. Therefore, analysis of these constituents in the serum performed before exposure to the food or chemical substance in question provides a base line observation against which any changes caused by the incubation of the cells with the food or chemical substance can be evaluated. Accordingly, analyzing for a given analyzable constituent of the leukocytes twice, once with and once without a challenge by the incriminated food or chemical, and comparing the results provides a reliable indication of the sensitivity to the challenging food or chemical.

The incriminated food or chemical is prepared for incubation with the leukocytes by any procedure known in the art including those used in the cytotoxic food test. For example, 5 ml of distilled water can be added to 5 ml of powdered food extract, the solution stirred for 10 minutes and allowed to stand for 24 hours. The supernatant is separated, filtered and then used as the food extract in a suitable dilution determined by titration studies. In general, dilutions of 1:4 to 1:6 are suitable for use in the present invention. It should be recognized that different dilutions can be used to change the sensitivity of the test when working with various foods and chemical substances.

The leukocytes to be challenged can be used as a solution or a suspension in any convenient carrying fluid, and, most conveniently, blood plasma is used to form a suspension of the cells. For example, the 15 ml of venous blood can be drawn into a heparinized vacutainer tube, centrifuged for 0.5–1.5 hours and the plasma and buffy coat aspirated. To eliminate the interference in the test results that may result from the lysis of erythrocytes inadvertently aspirated with the buffy coat, it is preferred to add 0.5 ml of red cell lysing solution (LAS reagent). The specimen can then be spun down and an aliquot of plasma taken for assay of the various enzymes or other component selected to serve as the base line value.

The polymorphonuclear cells in the buffy coat are mixed well with the patient's own plasma to form the cell suspension. This suspension can be used at full strength or in dilutions of 1:2 to 1:8. It is preferred to incubate approximately equal volumes of the food extract and the cell suspension at about room temperature for about 0.5–3 hours. Other volume ratios of the two fluids can be used, primarily depending on the dilutions of the two reactants, and any suitable amount of time which permits lysis of the cells to occur can be employed. Similarly, temperatures other than ambient can be employed provided that they permit lysis. After the incubation period, the cell suspension is centrifuged and the supernatant plasma removed for enzyme or other component assays.

The assays of the enzymes or other cell components employ standard methodology and are well known in the art. Accordingly, no detailed description of such assays will be set forth. At present, it is preferred to spectrophotometrically assay one or more of the LDH, SGOT, SGPT, gamma glutamyl transpeptidase or betahydroxybutyric dehydrogenase enzymes. Assays of SGOT, SGPT and LDH, alkaline phosphatase are most preferred because of their concentration in the cells.

In accordance with standard assay methodology, a negative control employing a cell suspension of an individual without any history of food allergy is usually performed with each batch of test samples. In addition to such negative controls, several internal negative controls are usually forthcoming when testing a battery of food extracts by the negative test results obtained with foods and chemical substances included in the panel.

In considering the results of the assays, the present in vitro test is considered a negative when the enzyme or other assayable constituent levels in the sample after incubation with the food allergen or chemical is not greater than two standard deviations of the values obtained with the sample before incubation with the incriminated food or chemical substance, and the values obtained with known negative controls. A change in the level between 2 and 3 standard deviations from the mean value is considered equivocal and changes of 3 or more standard deviations after incubation is considered a positive indication of allergy or intolerance. In order to minimize the risk of false results in this test, it is preferred to assay for at least two assayable constituents of the luekocytes and to consider the test positive when the levels of at least two of such constituents rise by more than 3 standard deviations after challenge with the suspected substance.

EXAMPLE

Enzyme concentrations in plasma of patients with food allergy before and after incubation with the incriminated food extract.

|  | BEFORE | AFTER |
|---|---|---|
| SGOT | 14 | 25 |
| SGPT | 16 | 45 |
| LDH | 112 | 124 |
| HDBD | 224 | 271 |
| YGT | 21 | 26 |

Various changes can be made in the process of this invention without departing from the spirit and scope thereof. The various embodiments which have been set forth herein were for the purpose of further illustrating the invention but were not intended to limit it.

We claim:
1. A method of determining a food or chemical allergy or intolerance in a human individual comprising:
   (a) incubating a suspension of the individual's polymorphonuclear leukocytes with the food or the chemical suspected of causing an allergy or intolerance;
   (b) assaying the supernatant of said suspension for an intracellular constituent of said leukocytes, said constituent being released to the supernatant due to lysis of the leukocytes in a positive test; and
   (c) comparing the results of step (b) with the results of an assay of a second suspension of the individual's leukocytes which is unchallenged by the given food or chemical.
2. The method of claim 1 wherein said leukocyte suspension is divided into at least two portions and one of said portions is incubated with said food or chemical before said assay.
3. The method of claim 2 wherein said leukocyte suspension is a suspension in plasma.
4. A method of claim 3 wherein said suspension is at a dilution of 1:2–1:8 w/v.
5. The method of claim 3 wherein said food or chemical is employed as an aqueous solution.
6. The method of claim 5 wherein said food or chemical is at a dilution of about 1:4–1:16 w/v.
7. The method of claim 6 wherein said leukocyte suspension is at a dilution in said suspension of about 1:2–1:8 w/v.
8. The method of claim 5 wherein equal volumes of said suspension and aqueous solution are incubated for about 0.5–3 hours at ambient temperature.
9. The method of claim 8 wherein at least two constituents of said leukocytes are assayed.
10. The method of claim 9 wherein said constituents are SGOT and SGPT.

* * * * *